United States Patent [19]

Smith et al.

[11] Patent Number: 4,572,189

[45] Date of Patent: Feb. 25, 1986

[54] ELECTRONIC CONTROLLER FOR USE WITH A SURGICAL LASER SYSTEM

[76] Inventors: Chadwick F. Smith, 1127 Wilshire Blvd., Los Angeles, Calif. 90017; Walter E. Johansen, III, 11661 San Vicente Blvd., both of Los Angeles, Calif. 90049

[21] Appl. No.: 540,299

[22] Filed: Oct. 11, 1983

[51] Int. Cl.$^4$ .................................................... A61N 5/06
[52] U.S. Cl. ............................. 128/395; 219/121 LA; 219/303
[58] Field of Search ........................................ 128/4–8, 128/303.1, 395–398; 219/121 LA; 372/25, 26

[56] References Cited

U.S. PATENT DOCUMENTS

| | | | |
|---|---|---|---|
| 4,074,719 | 2/1978 | Semm | 128/303.1 |
| 4,201,905 | 5/1980 | Clarke et al. | 219/121 LA |
| 4,232,678 | 11/1980 | Skovajsa | 128/395 |
| 4,309,998 | 1/1982 | Aron nee Rosa et al. | 128/395 |

*Primary Examiner*—Edward M. Coven
*Assistant Examiner*—Max F. Hindenburg

[57] ABSTRACT

The present invention is an electronic controller for use with a laser system which includes a mechanical triggering device and which generates a beam of light energy in the infrared spectrum. The electronic controller includes a laser modulator which turns the laser system on and off at a frequency rate of two hundred cycles per second and a trigger/reset circuit which is electrically coupled to the mechanical triggering circuit. The trigger/reset circuit provides a trigger signal in its triggered state and a reset signal in its untriggered state. The electronic controller also includes a clock circuit which is electrically coupled to the triggering circuit and which provides clock signals in response to the trigger signal and a one-shot monostable, multivibrator circuit having an RC timing circuit which is electrically coupled to the clock circuit and which controls the pulse width of its output signal in a range of 0.005 seconds and 0.1 seconds in response to the clock signals. The electronic controller further includes a counter which is electrically coupled to the one-shot monostable, multivibrator circuit and which counts each of the clock signals and a comparator which is electrically coupled to the counter in order to compare the number of the counted clock signals to a selected number and to the clock circuit and which is electrically coupled to the clock circuit, so that, when the number of the counted clock signal equals said selected number, the comparator provides a clock inhibit signal in order to inhibit the clock circuit from providing any more clock signals.

2 Claims, 4 Drawing Figures

ELECTRONIC CONTROLLER FOR USE WITH A SURGICAL LASER SYSTEM

BACKGROUND OF THE INVENTION

1. Field of the Invention

The present invention relates to an electronic controller for a surgical laser system and more particularly to an electronic controller which not only controls the pulse width of a beam of light energy from a surgical laser system a within a range of 0.005 seconds to 0.100 seconds, but also limits the maximum number of pulses to a number which a surgeon may select for use in surgical procedures.

2. Description of the Prior Art

U.S. Pat. No. 3,982,541, entitled Eye Surgical Instrument, issued to Francis A. L'Esperance on Sept. 28, 1976, teaches a method of surgically removing body tissue which includes the steps of contacting the body tissue with a probe open at a free end, passing a $CO_2$ laser beam through a central passage in the probe and the open end to the tissue at a power level sufficient to affect vaporization of tissue, vaporizing only the surface portion of the tissue exposed to the $CO_2$ laser beam in a manner so that the vaporizing step is surface phenomena at a depth not more than about 0.33 millimeters, introducing a gas stream into the probe downstream from the lenses associated with the $CO_2$ laser beam, passing the gas stream through the probe in a direction towards the free end of the probe and out of the probe, and removing smoke and any vaporized portion of the tissue through the probe by way of the gas stream.

U.S. Pat. No. 4,122,853, entitled Infrared Laser Photocautery Device, issued to Michael R. Smith on Oct. 31, 1978, teaches an apparatus and a method for cauterizing biological tissue while providing isolation from surrounding absorbing tissue and fluid media. The device includes a probe having a special window through which an infrared laser beam is directed to cauterize the biological tissue. The device also includes an infrared laser beam generator, a control circuit for controlling the intensity and duration of the laser beam and an articulating arm for directing the laser beam to the probe. The probe includes a hollow, laser light guide tube which has an infrared transparent window in its tip which permits the tip to be brought into contact with biological tissue to be cauterized while excluding the surrounding absorbing tissue from the effects of the beam.

In their article, entitled "The Use of the Laser in Neurological Surgery," published in *Surgical Neurology*, Volume 14, Number 1, pages 1-10, July, 1981, Myles L. Saunders, Harold F. Young, Donald P. Becker, Richard P. Greenberg, Pauline G. Newlon, Richard L. Corales, William T. Ham, and John T. Povlishock discuss the use of a $CO_2$ laser system in neurological surgery.

U.S. Pat. No. 3,710,798, entitled Laser System for Microsurgery, issued to Herbert C. Bredemeier on Jan. 16, 1973, teaches a laser system for microsurgery which includes a mirror for changing the direction of a beam of light energy from a $CO_2$ laser system and directing the beam to the treatment site.

U.S. Pat. No. 4,169,251, teaches Waveguide Gas Laser with High Freqency Transverse Discharge Excitation, issued to Katherine D. Laakman on Sept. 25, 1979, teaches a waveguide laser which is excited by means of a transverse discharge at radio frequencies generally in the vhf-uhf range, i.e., from about 30 MHz to about 3 GHz. These excitation frequencies are sufficiently high to ensure negligible interaction of discharge electrons with the discharge-establishing electrodes, thereby achieving superior discharge properties which result in a laser of improved performance and reduced size and complexity.

In their article, entitled "A Flexible Sealed Tube Transverse Radio Frequency Excited Carbon Dioxide Laser for Dermatologic Surgery," published in *Lasers in Surgery and Medicine*, Volume 2, Number 4, pages 317–332, 1983, Leon Goldman, Edward Perry, David Stefanovsky discuss a $CO_2$ laser system which has been found effective for dermatological surgery. The $CO_2$ laser system is a radio frequency transversely excited waveguide $CO_2$ laser systems.

In their article, entitled "Arterial response to laser operation for removal of atherosclerotic plaques," published in *The Journal of Thoracic and Cardiovascular Surgery*, Volume 85, Number 3, pages 409–421, March, 1983, Ross G. Gerrity, Floyd D. Loop, Leonard A. R. Golding, L. Allen Erhart, and Zsolt B. Argenyi, report that they have performed a series of experiments on using a beam of light energy from a $CO_2$ surgical laser system, which is Coherent's System 400, to vaporize plaque in coronary arteries of swines. They have used a beam of light energy having a diameter of 0.9 millimeters. They have varied the power of the beam of light energy from 10.0 watts to 40.0 watts for exposed time periods between 0.1 second and 1.0 second. They have used amounts of energy ranging from 1.0 joule to 40.0 joules. When they have used 1.0 joule of energy, they have vaporized 0.15 cubic millimeters of plaque material.

In order to understand the theory of operation of the controller it is necessary to understand the following set of theoretical and experimental calculations for the use of the $CO_2$ laser system in surgery. The following definitions are used: d, which is the spot size, is the diameter of a beam of light energy; A is the area of the beam of light energy; P is the power of the beam of light energy; t is the total duration of the beam of light energy; $\Delta t$ is the pulse width of an increment of the beam of the light energy; $\Delta l$ is the cutting depth of an increment of beam of light energy; $\Delta V$ is the volume of tissue vaporized by the increment of the beam of light energy and equals area of the beam of light energy multiplied by cutting depth of an increment of the beam of light enegy, $A\Delta l$.

The intensity, I, of the beam of light energy equals power divided by area, P/A. The amount of energy, E, delivered by the beam of light energy equals power multiplied by the total duration, Pt. The amount of energy, $\Delta E$, delivered by an increment of the beam of light energy equals power multiplied by its pulse width, $P\Delta t$. The energy density, R, is the amount of energy which is delivered by the increment of the beam of light energy divided by the volume of tissue in vaporized by the increment of the beam of light energy, $\Delta E/\Delta V$.

In their article, entitled "Laser Energy in Arthoscopic Meniscectomy," published in *Orthopedics*, Volume 6, Number 9, pages 1165–1169, September, 1983, Terry L. Whipple, Richard B. Caspari and John F. Meyers discuss the rationale and technique for performing arthoscopic meniscectomy with a carbon dioxide laser. They present findings of limited rabbit and human studies. They have used a $CO_2$ laser system, which is similar to the one which Gerrity et al, supra, have used and which provides a two millimeter spot size at a power setting varying between ten and ninety watts, to vaporize a portion of the meniscus. They have used the $CO_2$ laser system at a power setting of thirty watts having a pulse duration of 0.2 seconds to provide six joules of light energy in order to produce a crater which is two millimeters in diameter and which is 1.5 millimeters in depth. The volume of tissue which they have vaporized is 4.71 cubic millimeters.

In chapter 15, entitled "Basic principles arthoscopic surgery," of his book, entitled *Diagnostic and Surgical Arthoscopy: The Knee and Other Joints,* published by The C. V. Mosby Company, 1981, Lanny L. Johnson discusses the principles of arthoscopic surgery including proper techniques, proper portals of entry, the types of arthoscope to be utilized in the triangulation technique. He stresses that arthoscopic surgery decreases the morbidity over standard arthrotomy procedure.

In chapter 16, entitled, "Meniscal surgery," of his book, Johnson delineates the type of meniscal surgery. He bases the type of arthoscopic surgery necessary on the location of the tear, the extent of the tear and the nature of the adjacent joint. He stresses excising a minimal amount of the meniscus so that the remaining essentially normal meniscus can function biomechanically as a "washer" and "stabilizer" between the tibia and femur.

U.S. Pat. No. 4,369,768, entitled Arthoscope, issued to Marko Vukovic on Jan. 25, 1983, teaches an arthoscope.

U.S. Pat. No. 4,289,132, entitled Surgical Instrument and Method of Using the Same, issued to Robert D. Rieman on Sept. 15, 1981, teaches a surgical instrument which has a slender rod with a sharp point which is pushed inside out through skin tissue at a location remote from an incision so that the rod can be manipulated to perform a surgical procedure at the remote location by means of a surgical tool mounted on the other end of the rod.

U.S. Pat. Nos. 3,221,744, 3,835,859 and 4,067,340 teach surgical instruments for performing the posterior detachment of the meniscus which are relatively difficult to use and sometime fail to provide the desired detachment of the posterior part of the meniscus. The stopping of active bleeding, or hemostasis, is very difficult to achieve in a meniscectomy because of the inaccessibility of the posterior portion of the knee joint. Thus a meniscectomy is almost always performed with a tourniquet on the upper thigh and the tourniquet is not released until the surgical operation has been completed and a dressing and a compressive bandage applied to the knee joint which usually fills with blood. This postoperative bleeding contributes to the patient's pain and discomfort and the slowing of post-operative recovery.

In their article, entitled "Long-term clinical assessment of the efficacy of adjunctive coronary endarterectomy," published in *The Journal of Thoracic and Cardiovascular Surgery,* Volume 81, Number 1, pages 21-29, January 1981, D. Craig Miller, Edward B. Stinson, Philip E. Oyer, Bruce A. Reitz, Stuart W. Jamieson, Ricardo J. MorenoCabral and Norman E. Shumway demonstrate in a retrospective review the efficacy of right coronary endarterectomy. In their study they have found that the long-term survival following endarterectomy to be not statistically different from patients undergoing coronary bypass surgery alone. Despite a two-fold increase in the perioperative infarction rate with coronary endarterectomy, they have observed no differences in early mortality.

In their paper, entitled "Laser Endarterectomy in Vivo," Paper Number 1465 of Abstracts, published in *Circulation,* Supplement II, page II-366, October, 1982, Michael R. Treat, Francis M. Weld, John White, Kenneth A. Forde, John Fenoglio, Francis A. L'Esperance and Arthur B. Voorhees report they have studied the degree of injury and rate of healing of the arterial intima in New Zealand white rabbits. They have used a $CO_2$ laser system to produce a beam of light energy having a power intensity of 2.0 to 20.0 watts per square millimeters for a duration of 0.100 second to create an intimal crater. They have demonstrated that vascular injury has consisted of (1) an impact crater and (2) an adjacent zone of necrosis and that, if the zone of necrosis is sufficiently large, then thrombosis will occur within 24 hours. They have also demonstrated that intitmal healing is remarkably complete if thrombosis is avoided.

In their article, entitled "Effects of Carbon Dioxide, Nd-YAG, and Argon Laser Radiation on Coronary Atheromatous Plaques," published in the Section on Coronary Heart Disease, *The American Journal of Cardiology,* Volume 50, Number 6, pages 1199-1205, December, 1982, George S. Abela, Sigurd Normann, Donald Cohen, Robert L. Feldman, Edward A. Geiser and C. Richard Conti have reported their study of the comparative effects of light energy from different types of laser systems. They have demonstrated that the degree of arterial injury correlates with the total energy delivered. Total energy in joules is calculated by the product of the amount of power in watts and the duration of the exposure time in seconds. They have used a $CO_2$ laser system, a Nd:YAG laser system, and an Argon laser system. Irrespective of the wavelength of light energy there are three zones of arterial injury which occur. Tissue vaporization causes the first zone which is an impact crater. The second zone is a region of thermally induced necrosis and coagulation exist between 5 to 15 microns. The third zone is a region of acoustic and shock injury up to 30 microns.

U.S Pat. No. 3,730,185, entitled Endarterectomy Apparatus, issued to William Cook and Everett R. Lerwick on May 1, 1973, teaches an apparatus for removing arteriosclerotic material from an artery.

U.S Pat. No. 3,730,185, entitled Endarterectomy Apparatus, issued to Albert K. Chin on Sept. 22, 1981, teaches a center pull cutting annulus which is radially expansible to achieve complete removal of arteriosclerotic material from occluded arteries.

U.S. Pat. No. 3,929,238, entitled Sub-Intimal Dissection and Methods for Performing Endarterectomies Therewith, issued to Eli Curt on Dec. 30, 1975, teaches a sub-intimal dissector for removing arteriosclerotic material from an occluded artery.

U.S. Pat. No. 4,207,874, entitled Laser Tunnelling Device, issued to Daniel S. J. Choy on June 17, 1980, teaches to pass light energy from an Argon laser system into the artery of interest. The Argon laser system has been used with a power output is 4.5 watts and an exposure time of 36 seconds and has been found to be effective in restoring a 1.0 centimeter lumen in a completely thrombosed femoral artery.

U.S. Pat. No. 3,865,113, entitled Laser Device Particularly Useful as Surgical Scalpel, issued to Uzi Sharon and Isaac Kaplan on Feb. 11, 1975, teaches a laser beam manipulator including a tube which is optically coupled through an articulated arm to a $CO_2$ laser system and a beam targeting member which is carried by the tube.

U.S. Pat. No. 4,226,548, entitled Apparatus For and Method of Utilizing Energy to Excise Pathological Tissue, issued to S. K. Davi on May 12, 1982, teaches a collimator which is optically coupled through an articulated arm to a CO laser system and which reduces the cross-section of a beam of light energy from the $CO_2$ laser system.

In their article, entitled "Arterial response to laser operation for removal of atherosclerotic plaques," Gerrity et al have provided the following experimental values: P equals 10.0 watts; $\Delta t$ equals 0.1 second; $\Delta E$ equals 1.0 joule; the depth of the burn crater, $\Delta 1_b$, equals 0.1 millimeter; the area of tbe burn crater, $A_b$, equals 1.5 square millimeters; the volume of the burn crater vaporized by 1.0 joule of energy, $\Delta V_b$, equals 0.15 cubic millimeters. The energy density wbich is defined by the equation, $R = \Delta E / \Delta V_b$, equals 6.67 joules per cubic millimeters. The beam diameter, d, equals 0.9 millimeters; the beam area, A, equals 0.636 millimeters so that the beam intensity which is defined the equation $I = P/A$, equals 15.72 watts per square millimeters.

SUMMARY OF THE INVENTION

In view of the foregoing factors and conditions which are characteristic of the prior art it is the primary object of the present invention to provide for a surgical laser system an electronic controller which not only controls the pulse width of a beam of light energy from a surgical laser system within a range of 0.005 seconds to 0.100 seconds, but also limits the maximum number of pulses to a number which a surgeon may select for use in surgical procedures.

It is another object of the present invention to provide for a surgical laser system an electronic controller for use in arthoscopic surgical procedures, such as a meniscectomy, at locations remote and relatively inaccessible from an incision in order to perform a nonmechanically cutting the posterior attachments of a menicus or cartilage in a knee.

It is still another object of the present invention to provide for a surgical laser system an electronic controller for use in arthoscopic surgical procedures, such as a meniscectomy, which an orthopedic surgeon can not only perform more exactly and more quickly with substantially less trauma than he can with the prior art surgical instruments, but he can also obtain substantial hemostasis in meniscectomy thereby reducing post-operative discomfort and rehabilitation time of a patient.

It is still yet another object of the present invention to provide for a surgical laser system an electronic controller for use in arthoscopic surgical procedures, such as a meniscectomy, which an orthopedic surgeon can vaporize a posterior portion of the meniscus from the synovium and ligament by means of a beam of light without any trauma to the remaining portion of the meniscus at positions remote and relatively inaccessible from an incision.

It is yet still another object of the present invention to provide for a surgical laser system an electronic controller for use in cardiovascular surgical procedures, such as a coronary endarterectomy, when used either as an adjunct or an alternative to coronary bypass surgery, which a cardiovascular surgeon can vaporize plaque in the coronary artery by means of a beam of light without any trauma to the coronary artery.

In accordance with the preferred embodiment of the present invention an electronic controller for use with a laser system which includes a mechanical triggering device and which generates a beam of light energy in the infrared spectrum is described. The electronic controller includes a laser modulator which turns the laser system on and off at a freqency rate of two hundred cycles per second and a trigger/reset circuit which is electrically coupled to the mechanical triggering circuit. The trigger/reset circuit provides a trigger signal in its triggered state and a reset signal in its untriggered state. The electronic controller also includes a clock circuit which is electrically coupled to the triggering circuit and which provides clock signals in response to the trigger signal and a one-shot monostable, multivibrator circuit having an RC timing circuit which is electrically coupled to the clock circuit and which controls the pulse width of its output signal in a range of 0.005 seconds and 0.1 seconds in response to the clock signals. The electronic controller further includes a counter which is electrically coupled to the one-shot monostable, multivibrator circuit and which counts each of the clock signals and a comparator which is electrically coupled to the counter in order to compare the number of the counted clock signals to a selected number and to the clock circuit and which is electrically coupled to the clock circuit, so that, when the number of the counted clock signal equals said selected number, the comparator provides a clock inhibit signal in order to inhibit the clock circuit from providing any more clock signals.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE PREFERRED EMBODIMENT

Figure 1:
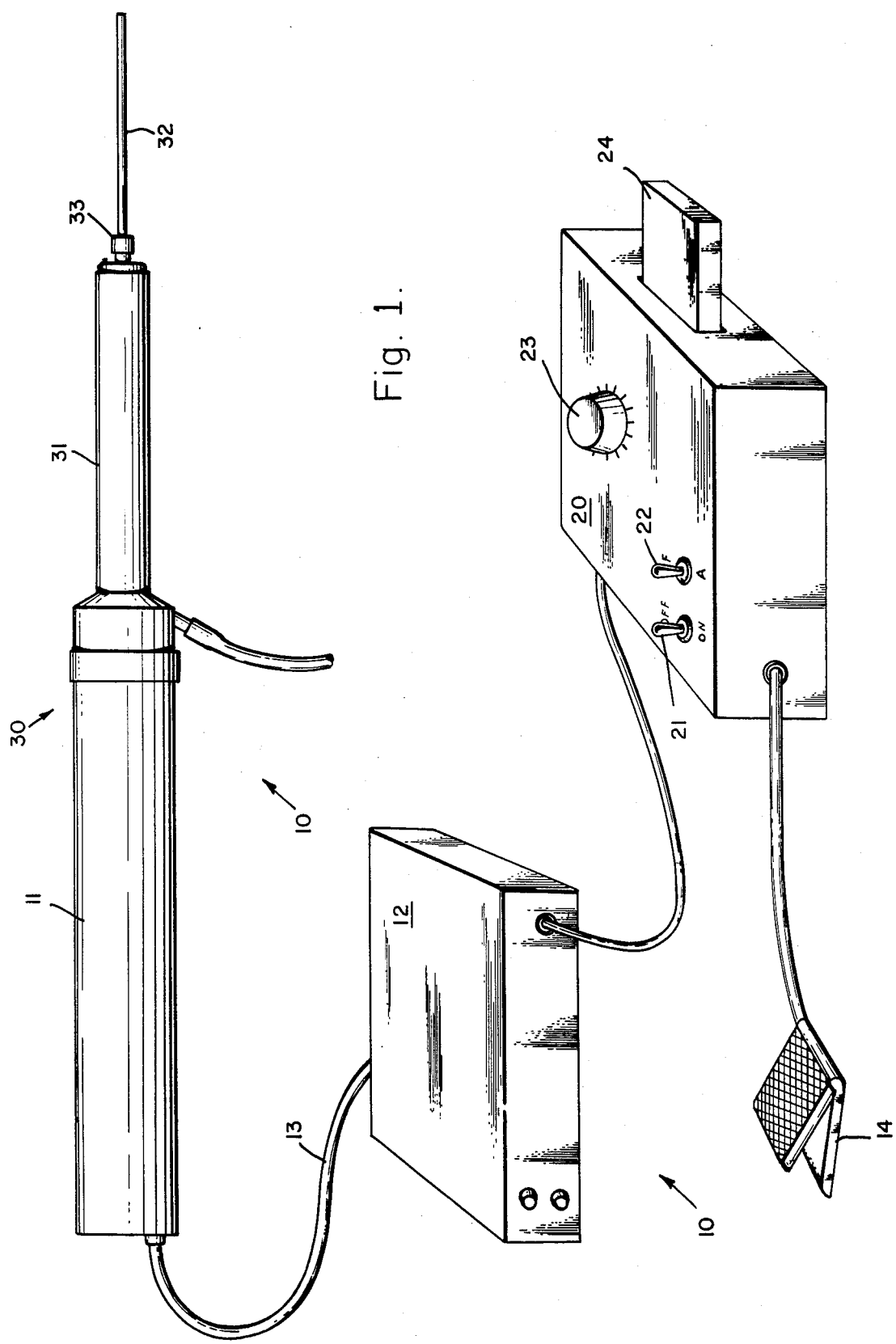
FIG. 1 is a perspective drawing of a hand held laser system and an coronary introducer and a schematic drawing of a power supply and an electronic controller which has been constructed in accordance with the principles of the preferred embodiment of the present invention.

In order to best understand the present invention it is necessary to refer to the following description of its preferred embodiment in conjunction with the accompanying drawing. Referring to FIG. 1 a hand-held laser system 10 includes a laser bore and electrode structure 11, a power supply 12 which is a radio frequency generator and a coaxial connector 13 which electrically couples the power supply 12 to the laser bore and electrode structure 11. A foot switch 14 is electrically coupled to the power supply 12 through an electronic controller 20 which may be used in combination with the hand-held laser system 10 to control the pulse width of a beam of light energy from the hand-held laser system 10 within a range of 0.005 seconds to 0.100 seconds and to limit the maximum number of pulses to a number which a surgeon may select for use in surgical procedures. The electronic controller 20 has an on/off switch 21, a pulse width setting switch 22 and a selector switch 23 for selecting the number of pulses. The electronic controller 20 may also have a cartridge 24 which contains a programmable read only memory (PROM). The hand-held laser system 10 has a cornary introducer 30 which is mechanically and optically coupled to the laser bore and electrode structure 11 so that it delivers an increment of light energy during each pulse over a duration of the pulse width.

Figure 2:
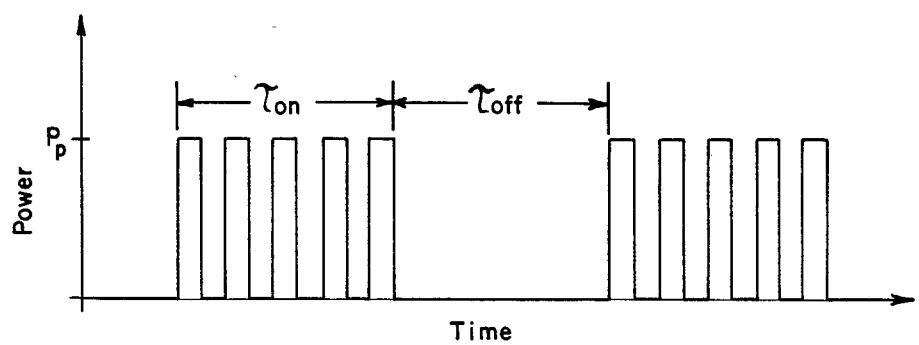
FIG. 2 is a schematic drawing of a first pulse modulation scheme of the power supply for the hand-held laser system of FIG. 1 in order to control the average amount of power which is contained in each pulse width.

Referring to FIG. 2 a first pulse modulation scheme of the power supply 12 for the hand-held laser system 10 of FIG. 1 controls the average of power, $P_a$, which occurs over the duration, $\Delta t$, of each pulse width and which is defined by the equation: $P_a = P_p(\tau_{on}/\tau_t)$ where $P_p$ equals peak power and the equation, $\tau_t = \tau_{on} + \tau_{off}$, defines the period of the duty cycle of the power supply 12.

Figure 2A:
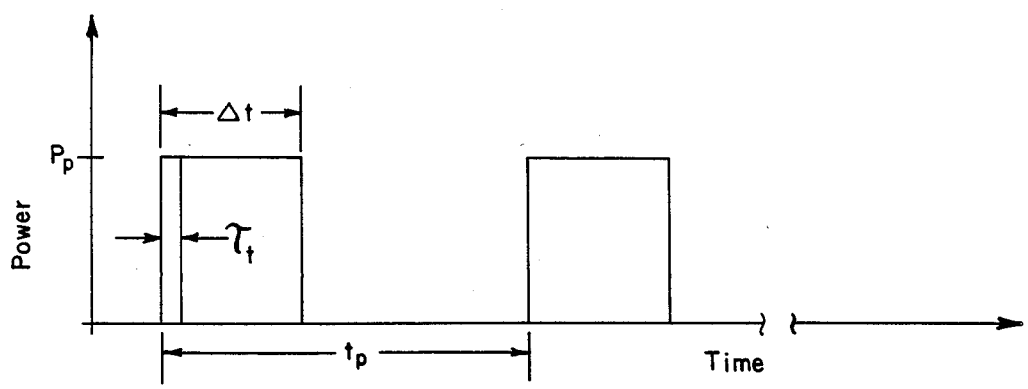
FIG. 2a is a schematic drawing of a second pulse modulation scheme which the electronic controller provides to the power supply for the hand-held laser system of FIG. 1 in order to control the duration of each pulse width.

Referring to FIG. 2a a second pulse modulation scheme which the electronic controller 20 provides to the power supply 12 for the hand-held laser system of FIG. 1 controls the duration of each pulse width, $\Delta t$, over a time period, $t_p$, which is the period of each pulse cycle. The period of each pulse is much greater than the period of the duty cycle of the power supply 12, i.e. $t_p >> \tau_t$.

When the coronary introducer 30 is used, the hand-held $CO_2$ laser system 10 removes a disc of tissue with each output pulse of light energy. The diameter of each disc of tissue is same as the inner diameter of the coronary introducer. The length of each disc of tissue is 0.1 millimeter.

Leroy V. Sutter, Jr., has filed an application, which the inventors hereby incorporate it by reference, entitled An Improved Coupling Circuit for Use with a Transversely Excited Gas Laser, having Ser. No. 370,103, filed Apr. 20, 1982, which teaches an improved coupling circuit for use in combination with a gas laser including a laser bore and electrode structure.

The hand-held $CO_2$ laser system 10 delivers an output beam of light energy into a coronary artery through the coronary introducer 30 in order to remove plaque. In using the hand-held $CO_2$ laser system 10 with the coronary introducer 30 the electronic controller 20 is set at a pulse width of 0.0333 seconds for hard plaque at P equals 15.0 watts so that $\Delta E$ equals 0.5 joules and $\Delta l$ equals 0.1 millimeter. The beam diameter, d, equals 1.0 millimeter and the beam area, A, equals 0.8 square millimeters. The volume of tissue vaporized by 0.5 joules of energ equals 0.08 cubic millimeters so that the energy density, $R = \Delta E/\Delta V$, equals 6.25 joules per cubic millimeters and intensity, $I = P/A$, equals 18.75 watts per square millimeters.

The $CO_2$ hand-held laser system 10 is used for performing coronary endarterectomy. The hand-held laser systems 10 provides an output beam of light energy which can be focused to a beam diameter in the range of 0.5 to 1.0 millimeter. The hand-held laser system 10 provides pulsed power with the duration of each output pulse being in the range of 0.005 to 0.100 seconds. The electronic controller 20 has an aggressive cutting mode, A, and a fine cutting mode, F. The selection of one of the two cutting modes determines the duration of each output pulse of the beam of light energy. The selector switch 23 sets the number of output pulses in a firing cycle of the hand-held $CO_2$ laser system. Either the aggressive cutting mode or the fine cutting mode is set so that the number of output pulses in a firing cycle is proportional to the length of the plaque to be removed. When the duration of each output pulse is less than 0.050 seconds the duration of each output pulse determines the depth of the cut and the diameter of the output beam of light energy determines the diameter of the plaque vaporized.

Figure 3:
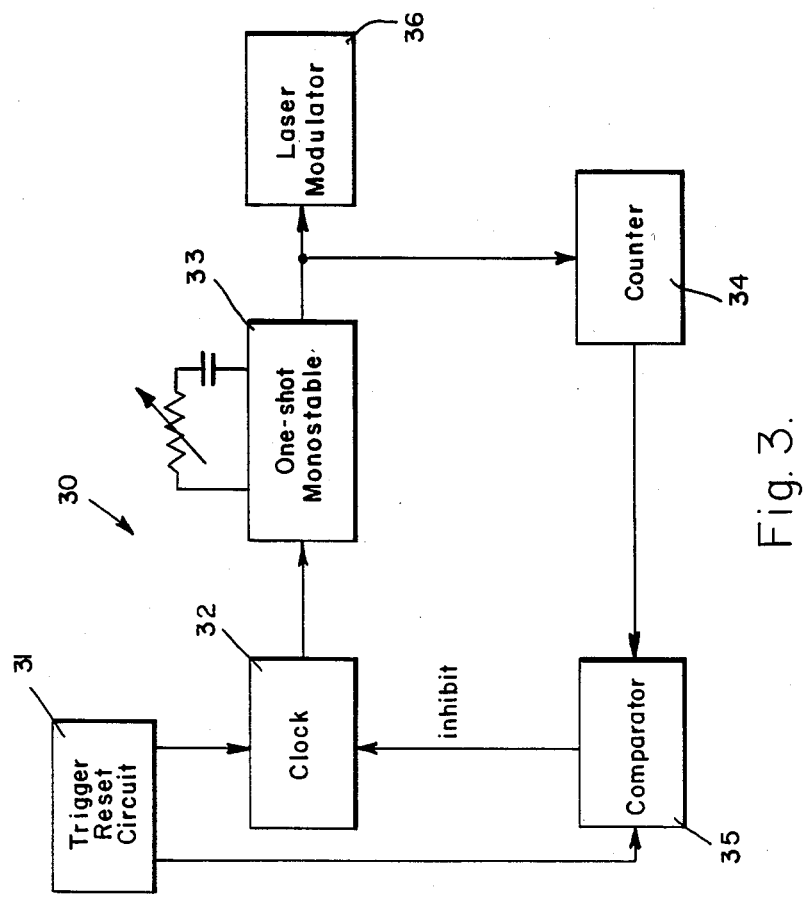
FIG. 3 is a detailed schematic drawing of the electronic controller of FIG. 1.

Referring to FIG. 3 the electronic controller 20 includes a trigger/reset circuit 31, a clock 32 which is electrically coupled to the trigger/reset circuit 31 which triggers the clock 32 and a monostable one-shot multivibrator 33 which is electrically coupled to the clock 32 and which has an RC circuit with a variable resistor to control the pulse width, $\Delta t$. The clock 32 triggers the monostable one-shot multivibrator 33 which is electrically ocupled to a counter 34. The electronic controller 20 also includes a comparator 35 which is electrically coupled to the counter 34 and to the clock 32 and which provides an inhibit signal to the clock 32. The monostable one-shot multivibrator 33 is electrically coupled to a laser modulation circuit 36 of the power supply 12 in order to provide a pulse signal so that the hand-held laser system 10 is able to deliver an incremental beam of light energy. The electronic controller 20 for the hand-held laser system 10 not only controls the pulse width of the beam of light energy within a range of 0.005 seconds to 0.100 seconds, but also limits the maximum number of pulses to a number which a surgeon may select for use in surgical procedures.

From the foregoing it can be seen that an electronic controller for a hand held laser system for use in surgery has been described. It should be noted that distances of and between the figures are not to be considered significant.

Accordingly it is intended that the foregoing disclosure and showing made in the drawing shall be considered only as an illustration of the principles of the present invention.

What is claimed is:

1. A combination of an electronic controller and a laser system which includes a mechanical triggering device and which generates a beam of light energy in the infrared spectrum and which is electrically coupled to said electronic controller so that said electronic controller not only controls the pulse width of said beam of light energy within a range of 0.005 seconds to 0.100 seconds, but also limits the maximum number of pulses to a number which a surgeon may select for use in surgical procedures, said electronic controller comprising:
   a. modulating means for turning said laser system on and off at a freqency rate of in the range of two hundred cycles per second to twenty cycles per second;
   b. a triggering circuit which is electrically coupled to said mechanical triggering circuit and which provides a trigger signal in its triggered state and a reset signal in its untriggered state;

c. a clock circuit which is electrically coupled to said triggering circuit and which provides clock signals in response to said trigger signal;

d. a one-shot monostable, multivibrator circuit having an RC timing circuit which is electrically coupled to said clock circuit and which controls the pulse width of its output signal in a range of 0.005 seconds and 0.1 seconds in response to said clock signals;

e. a counter which is electrically coupled to said one-shot monostable, multivibrator circuit and which counts each of said clock signals;

f. a comparator which is electrically coupled to said counter in order to compare the number of said counted clock signals to said number which the surgeon has selected and to said clock circuit and which is electrically coupled to said clock circuit, so that, when the number of said counted clock signal equals said number, said comparator provides a clock inhibit signal in order to inhibit said clock circuit from providing any more clock signals.

2. A combination of an electronic controller and a laser system according to claim 1 where a read only memory is electrically coupled to said triggering circuit in order to electronically preprogram a plurality of surgical procedures.

* * * * *